United States Patent
Chen et al.

(10) Patent No.: US 9,182,335 B2
(45) Date of Patent: Nov. 10, 2015

(54) METHOD FOR INSPECTING PANEL-BONDING SEMI-FINISHED PRODUCT

(71) Applicant: Shenzhen China Star Optoelectronics Technology Co., Ltd., Shenzhen, Guangdong (CN)

(72) Inventors: Fangfu Chen, Shenzhen (CN); Tao Ding, Shenzhen (CN); Guodong Zhao, Shenzhen (CN); Ming Liu, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 189 days.

(21) Appl. No.: 14/235,067

(22) PCT Filed: Jun. 28, 2013

(86) PCT No.: PCT/CN2013/078242
§ 371 (c)(1),
(2) Date: Jan. 26, 2014

(87) PCT Pub. No.: WO2014/180049
PCT Pub. Date: Nov. 13, 2014

(65) Prior Publication Data
US 2015/0268175 A1    Sep. 24, 2015

(30) Foreign Application Priority Data
May 8, 2013    (CN) .......................... 2013 1 0166741

(51) Int. Cl.
*G01N 21/00*    (2006.01)
*G01N 21/95*    (2006.01)
*G01N 21/88*    (2006.01)
*G01N 21/84*    (2006.01)

(52) U.S. Cl.
CPC ............ *G01N 21/00* (2013.01); *G01N 21/8803* (2013.01); *G01N 21/95* (2013.01); *G01N 2021/845* (2013.01); *G01N 2021/9513* (2013.01)

(58) Field of Classification Search
CPC .................. G01N 33/54366; G01N 33/54373; G01N 33/54386
USPC ................ 156/64, 60, 557, 245, 248, 249.11; 356/237.1–237.5, 400, 401, 453.11
See application file for complete search history.

(56) References Cited

U.S. PATENT DOCUMENTS

| | | | | |
|---|---|---|---|---|
| 7,830,502 B2 * | 11/2010 | Iwai | ..................... | G01N 21/896 356/237.4 |
| 2012/0125516 A1 * | 5/2012 | Wechsler | .............. | B29C 44/306 156/60 |

FOREIGN PATENT DOCUMENTS

| | | |
|---|---|---|
| CN | 101324713 A | 12/2008 |
| CN | 101571628 A | 11/2009 |
| CN | 102062737 A | 5/2011 |
| JP | 2012163370 A | 8/2012 |

* cited by examiner

*Primary Examiner* — Kara E Geisel
*Assistant Examiner* — Iyabo S Alli
(74) *Attorney, Agent, or Firm* — Andrew C. Cheng (57) ABSTRACT

The present invention provides a method for inspecting a panel-bonding semi-finished product, which includes (1) placing a panel-bonding semi-finished product on a tray in a feeding station; (2) using a conveyance mechanism to convey the tray and the panel-bonding semi-finished product to a final display test station; (3) proceeding with a final display test on the panel-bonding semi-finished product and ending the test if the result fails and proceeding to the next step if the result passes; (4) conveying the tray and the panel-bonding semi-finished product to a final visual check station; (5) proceeding with final visual check for the panel-bonding semi-finished product that passes the final display test and if the result fails, ending the inspection and if the result passes, then proceeding to the next step; (6) conveying the tray and the panel-bonding semi-finished product to a quality inspection station; (7) proceeding with quality inspection on the panel-bonding semi-finished product; (8) conveying the tray and the panel-bonding semi-finished product to a packaging station; and (9) proceeding with packaging of the panel-bonding semi-finished product.

11 Claims, 4 Drawing Sheets

METHOD FOR INSPECTING PANEL-BONDING SEMI-FINISHED PRODUCT

BACKGROUND OF THE INVENTION

1. Field of the Invention

The present invention relates to the field of liquid crystal displaying technology, and in particular to a method for inspecting a semi-finished product of panel bonding.

2. the Related Arts

Liquid crystal displays have a variety of advantages, such as thin device body, low power consumption, and being free of radiation, and are thus widely used. Most of the liquid crystal displays that are currently available in the market are backlighting liquid crystal displays, which comprise a liquid crystal panel and a backlight module. The operation principle of the liquid crystal panel is that, with liquid crystal molecules interposed between two parallel glass substrates, a driving voltage is applied to the two glass substrates to control the rotation direction of liquid crystal molecules in order to refract out light emitting from the backlight module for generating images. Since the liquid crystal panel itself does not emit light, light must be provided by the backlight module in order to normally display images. Thus, the backlight module is one of the key components of a liquid crystal display. The backlight modules can be classified in two types, namely a side-edge backlight module and a direct backlight module, according to the position where light gets incident. The direct backlight module comprises a light source, such as a cold cathode fluorescent lamp (CCFL) or a light-emitting diode (LED), which is arranged at the backside of the liquid crystal panel to form a planar light source directly supplied to the liquid crystal panel. The side-edge backlight module comprises an LED light bar, serving as a backlight source, which is arranged at an edge of a backplane to be located rearward of one side of the liquid crystal panel. The LED light bar emits light that enters a light guide plate (LGP) through a light incident face at one side of the light guide plate and is projected out of a light emergence face of the light guide plate, after being reflected and diffused, to pass through an optic film assembly to form a planar light source for the liquid crystal panel.

In the contemporary liquid crystal display manufacturing industry, after a bonding process of a liquid crystal panel, a semi-finished of which circuitry has been bonded will be shipped to a client to allow the client to carry out assembly of the panel and a backlight board. As such, the operation cost of the company and the manufacture cost of the client can be lowered down. Thus, shipment by semi-finished products is now the main stream of sales in the industry.

Figure 1:
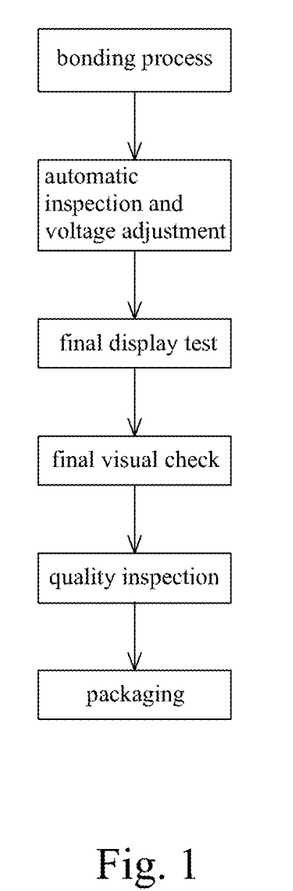
FIG. 1 is a flow chart illustrating a conventional operation process of inspection of a panel-bonding semi-finished product.

Referring to FIG. 1, heretofore, in the manufacturing of a semi-finished product of panel bonding, after the bonding operation, a tray and a cassette are used to bear a bonded product and an operator uses a cart to convey the semi-finished product to a display voltage adjustment and test station, where adjustment and test of voltage is carried out by using A P-gamma chip, and then conveyed to a final display (FD) test station to carry out operations of display checking, product classification evaluation, and posting. Afterwards, the operator moves the product to a packaging station to carry out operations of manual retrieval of panel, posting and barcode pasting, final visual (FV) check, quality inspection, panel disposition, packaging, and box barcode pasting, to thereby completing the processing of the semi-finished product before shipment.

However, during the manufacturing of a panel-bonding semi-finished product, various problems exit, including the test time carried out by using the P-gamma chip being long, making it not possible to satisfy the needs for test space of the P-gamma chip, all steps being not in synchronization with each other, and operators needing to wait, leading to low manufacture efficiency and insufficient throughput. With the increasing size expansion of the liquid crystal panel, the operation difficulty of operators will raised and various problems, such as panel breaking and damage of product caused by electro-static discharge (ESD), may occur during conveyance and pick-up and placing of panels and inspection operations of the panels, so that it is hard to ensure the yield rate of the semi-finished products. In light of these shortcomings, no improvement has been yet developed in the liquid crystal display manufacturing industry.

SUMMARY OF THE INVENTION

An object of the present invention is to provide a method for inspecting a panel-bonding semi-finished product, in which a conveyance mechanism is adopted to achieve automatization of an inspection line by jointing test of a semi-finished product of panel bonding to a main production line of a bonding operation of the panel-bonding semi-finished product, adding a barcode pasting machine and an automatic packaging machine, coordinating operations of various stations for synchronization, so as to satisfy the requirement for test with programmable gamma calibrating buffering circuit chip, allow operator to not contact the products, reduce operator labor required, and enhance yield rate and throughput of semi-finished products of panel bonding.

To achieve the above object, the present invention provides a method for inspecting a panel-bonding semi-finished product, which comprises the following steps:

(1) placing a panel-bonding semi-finished product on a tray in a feeding station;

(2) using a conveyance mechanism to convey the tray and the panel-bonding semi-finished product placed thereon to a final display test station;

(3) proceeding with a final display test on the panel-bonding semi-finished product and ending the test if the test fails and proceeding to the next step if the test passes;

(4) using the conveyance mechanism to convey the tray and the panel-bonding semi-finished product positioned thereon and passing the final display test to a final visual check station;

(5) proceeding with final visual check for the panel-bonding semi-finished product that passes the final display test and if the result of inspection fails, ending the inspection and if the result of inspection passes, then proceeding to the next step;

(6) using the conveyance mechanism to convey the tray and the panel-bonding semi-finished product positioned thereon and passing the final visual check to a quality inspection station;

(7) proceeding with quality inspection on the panel-bonding semi-finished product that passes the final visual check and if the result of inspection fails, ending the inspection and if the result of inspection passes, then proceeding to the next step;

(8) using the conveyance mechanism to convey the tray and the panel-bonding semi-finished product positioned thereon and passing the quality inspection to a packaging station; and (9) proceeding with packaging of the panel-bonding semi-finished product passing the quality inspection.

Step (1) comprises: carrying out de-packaging, posting, positioning, and conveyance of the panel-bonding semi-finished product and then placing the panel-bonding semi-finished product on the tray.

The conveyance mechanism comprises a double-plus chain conveyor mechanism.

The double-plus chain conveyor mechanism comprises a circulation conveyance. The circulation conveyance ladder comprises two parallel conductor tracks. The feeding station is located at one end of the circulation conveyance ladder and the packaging station is located at an opposite end of the circulation conveyance ladder. The final display test station, the final visual check station, and the quality inspection station are arranged sequentially between the feeding station and the packaging station. The final display test station comprises a plurality of final display test operation sites. The final display test operation sites are symmetrically set at two sides of the circulation conveyance ladder. The final visual check station comprises two final visual check operation sites that are arranged symmetrically on the two sides of the circulation conveyance ladder. Each of the final visual check operation sites comprises a barcode pasting machine. The quality inspection station comprises two quality inspection operation sites symmetrically set at the two sides of the circulation conveyance ladder. The packaging station comprises a first-rate product packaging state and a non-first-rate product packaging state respectively set at the two sides of the circulation conveyance ladder. The first-rate product packaging state and the non-first-rate product packaging state each comprise an automatic packaging machine.

The tray arranged on the double-plus chain conveyor mechanism and is movable with the double-plus chain conveyor mechanism and comprises a tray body and a P-gamma chip test transducer connected to the body. The tray body is provided with backlighting, a P-gamma chip signal generator, a relay contact, a P-gamma chip signal line, and two control buttons. The two control buttons are respectively an "activating tray backlighting button" and an "ejecting tray button".

Step (3) comprises: connecting the relay contact to the conductor tracks to proceed with the final display test and identifying and posting of display classification and if the result of the test fails, ending the inspection of the panel-bonding semi-finished product and if the result of test passes, connecting a P-gamma chip signal line of the tray to a circuit board of the panel-bonding semi-finished product and positioning at the same time a P-gamma chip test transducer at the middle of the panel-bonding semi-finished product and pressing down the "activating tray backlighting button" of the tray body to activate a function of the tray body to adjust and reach the most user-fit color and resolution through software based automatic inspection and voltage adjustment; and step (4) comprises: pressing down the "ejecting tray button" and conveying the tray and the panel-bonding semi-finished product placed on the tray to the final visual check station.

Step (5) comprises: inspecting a front appearance of the panel-bonding semi-finished product and if abnormality is identified, then carrying out a cleansing operation on the abnormality and if the abnormality is not cleanable, ending the inspection of the panel-bonding semi-finished product, if the abnormality is cleansed, a barcode machine being used to automatically paste a classification barcode according to the result of test of step (3) and after the tray body passes through the software based automatic inspection and voltage adjustment to reach the most user-fit color and resolution, removing the P-gamma chip signal line from the circuit board of the panel-bonding semi-finished product.

In step (9), an automatic packaging machine is used to carry out packaging according to display classification of the panel-bonding semi-finished product.

The circulation conveyance ladder comprises adjustment mechanisms that have functions of elevation, rotation, and conveyance and are arranged to respectively correspond to the final display test operation sites of the final display test station, the final visual check operation sites of the final visual check station, and the quality inspection operation sites of the quality inspection station. The adjustment mechanisms are operable to switch the locations of trays on the two sides of the circulation conveyance ladder.

The final display test station comprises six final display test operation sites. The six final display test operation sites are arranged at two sides of the circulation conveyance ladder in a symmetric manner. The conductor tracks supplies electrical power to the tray and electrical voltage provided by the conductor tracks is 12V or 24V.

The present invention also provides a method for inspecting a panel-bonding semi-finished product, which comprises the following steps:

(1) placing a panel-bonding semi-finished product on a tray in a feeding station;

(2) using a conveyance mechanism to convey the tray and the panel-bonding semi-finished product placed thereon to a final display test station;

(3) proceeding with a final display test on the panel-bonding semi-finished product and ending the test if the test fails and proceeding to the next step if the test passes;

(4) using the conveyance mechanism to convey the tray and the panel-bonding semi-finished product positioned thereon and passing the final display test to a final visual check station;

(5) proceeding with final visual check for the panel-bonding semi-finished product that passes the final display test and if the result of inspection fails, ending the inspection and if the result of inspection passes, then proceeding to the next step;

(6) using the conveyance mechanism to convey the tray and the panel-bonding semi-finished product positioned thereon and passing the final visual check to a quality inspection station;

(7) proceeding with quality inspection on the panel-bonding semi-finished product that passes the final visual check and if the result of inspection fails, ending the inspection and if the result of inspection passes, then proceeding to the next step;

(8) using the conveyance mechanism to convey the tray and the panel-bonding semi-finished product positioned thereon and passing the quality inspection to a packaging station; and (9) proceeding with packaging of the panel-bonding semi-finished product passing the quality inspection; and wherein step (1) comprises: carrying out de-packaging, posting, positioning, and conveyance of the panel-bonding semi-finished product and then placing the panel-bonding semi-finished product on the tray;

wherein the conveyance mechanism comprises a double-plus chain conveyor mechanism;

wherein the double-plus chain conveyor mechanism comprises a circulation conveyance, the circulation conveyance ladder comprising two parallel conductor tracks, the feeding station being located at one end of the circulation conveyance ladder and the packaging station being located at an opposite end of the circulation conveyance ladder, the final display test station, the final visual check station, and the quality inspection station being arranged sequentially between the feeding station and the packaging station, the final display test station comprising a plurality of final display test operation sites, the final display test operation sites being symmetrically set at two sides of the circulation conveyance ladder, the final visual check station comprising two final visual check operation sites that are arranged symmetrically on the two sides of the circulation conveyance ladder, each of the final visual check operation sites comprising a barcode pasting machine, the quality inspection station comprising two quality inspection operation sites symmetrically set at the two sides of the circulation conveyance ladder, the packaging station comprising a first-rate product packaging state and a non-first-rate product packaging state respectively set at the two sides of the circulation conveyance ladder, the first-rate product packaging state and the non-first-rate product packaging state each comprising an automatic packaging machine;

wherein the tray arranged on the double-plus chain conveyor mechanism and is movable with the double-plus chain conveyor mechanism and comprises a tray body and a P-gamma chip test transducer connected to the body, the tray body being provided with backlighting, a P-gamma chip signal generator, a relay contact, a P-gamma chip signal line, and two control buttons, the two control buttons being respectively an "activating tray backlighting button" and an "ejecting tray button";

wherein step (3) comprises: connecting the relay contact to the conductor tracks to proceed with the final display test and identifying and posting of display classification and if the result of the test fails, ending the inspection of the panel-bonding semi-finished product and if the result of test passes, connecting a P-gamma chip signal line of the tray to a circuit board of the panel-bonding semi-finished product and positioning at the same time a P-gamma chip test transducer at the middle of the panel-bonding semi-finished product and pressing down the "activating tray backlighting button" of the tray body to activate a function of the tray body to adjust and reach the most user-fit color and resolution through software based automatic inspection and voltage adjustment; and step (4) comprises: pressing down the "ejecting tray button" and conveying the tray and the panel-bonding semi-finished product placed on the tray to the final visual check station;

wherein step (5) comprises: inspecting a front appearance of the panel-bonding semi-finished product and if abnormality is identified, then carrying out a cleansing operation on the abnormality and if the abnormality is not cleanable, ending the inspection of the panel-bonding semi-finished product, if the abnormality is cleansed, a barcode machine being used to automatically paste a classification barcode according to the result of test of step (3) and after the tray body passes through the software based automatic inspection and voltage adjustment to reach the most user-fit color and resolution, removing the P-gamma chip signal line from the circuit board of the panel-bonding semi-finished product;

wherein in step (9), an automatic packaging machine is used to carry out packaging according to display classification of the panel-bonding semi-finished product;

wherein the circulation conveyance ladder comprises adjustment mechanisms that have functions of elevation, rotation, and conveyance and are arranged to respectively correspond to the final display test operation sites of the final display test station, the final visual check operation sites of the final visual check station, and the quality inspection operation sites of the quality inspection station, the adjustment mechanisms being operable to switch the locations of trays on the two sides of the circulation conveyance ladder; and wherein the final display test station comprises six final display test operation sites, the six final display test operation sites being arranged at two sides of the circulation conveyance ladder in a symmetric manner, the conductor tracks supplying electrical power to the tray, electrical voltage provided by the conductor tracks being 12V or 24V.

The efficacy of the present invention is that the present invention provides a method for inspecting a panel-bonding semi-finished product, which adopts a conveyance mechanism to achieve automatization of an inspection line, joints test operations of the panel-bonding semi-finished product to a main bonding line of the panel-bonding semi-finished product, adds barcode pasting machines and automatic packaging machines, make a P-gamma chip carrying out software based automatic inspection and voltage adjustment to reach the most user-fit color and resolution and in combination with a final display test and a final visual check, coordinate all operation stations to operate in synchronization with each other so as to satisfy the required P-gamma chip test of the industry, where the operators do not need to contact products so as to achieve the purposes of reducing labor and improving the product yield rate of the product throughput of the panel-bonding semi-finished product and also to meet the trend of development of large sizes, avoid influence of human factors on the product yield rate and product throughput, and increase economical advantage.

For better understanding of the features and technical contents of the present invention, reference will be made to the following detailed description of the present invention and the attached drawings. However, the drawings are provided for the purposes of reference and illustration and are not intended to impose limitations to the present invention.

BRIEF DESCRIPTION OF THE DRAWINGS

The technical solution, as well as other beneficial advantages, of the present invention will be apparent from the following detailed description of embodiments of the present invention, with reference to the attached drawing. In the drawing.

DETAILED DESCRIPTION OF THE PREFERRED EMBODIMENTS

To further expound the technical solution adopted in the present invention and the advantages thereof, a detailed description is given to a preferred embodiment of the present invention and the attached drawings.

Figure 2:
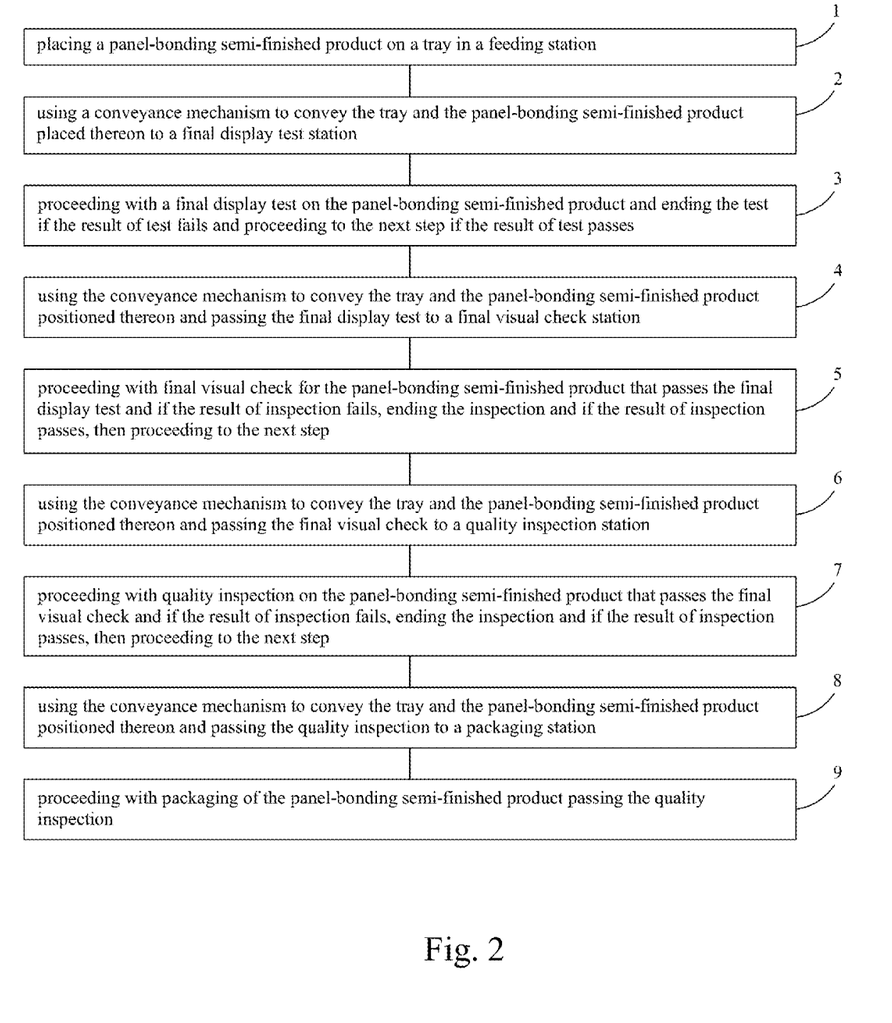
FIG. 2 is a flow chart illustrating a method for inspecting a panel-bonding semi-finished product according to the present invention.
Figure 3:
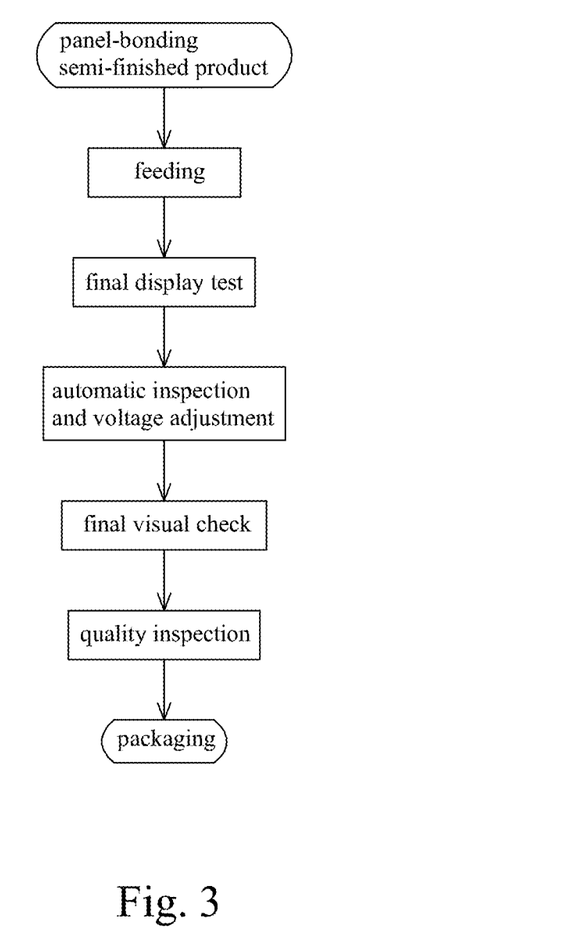
FIG. 3 is a flow chart illustrating the operation process of inspection of a panel-bonding semi-finished product according to the present invention.
Figure 4:
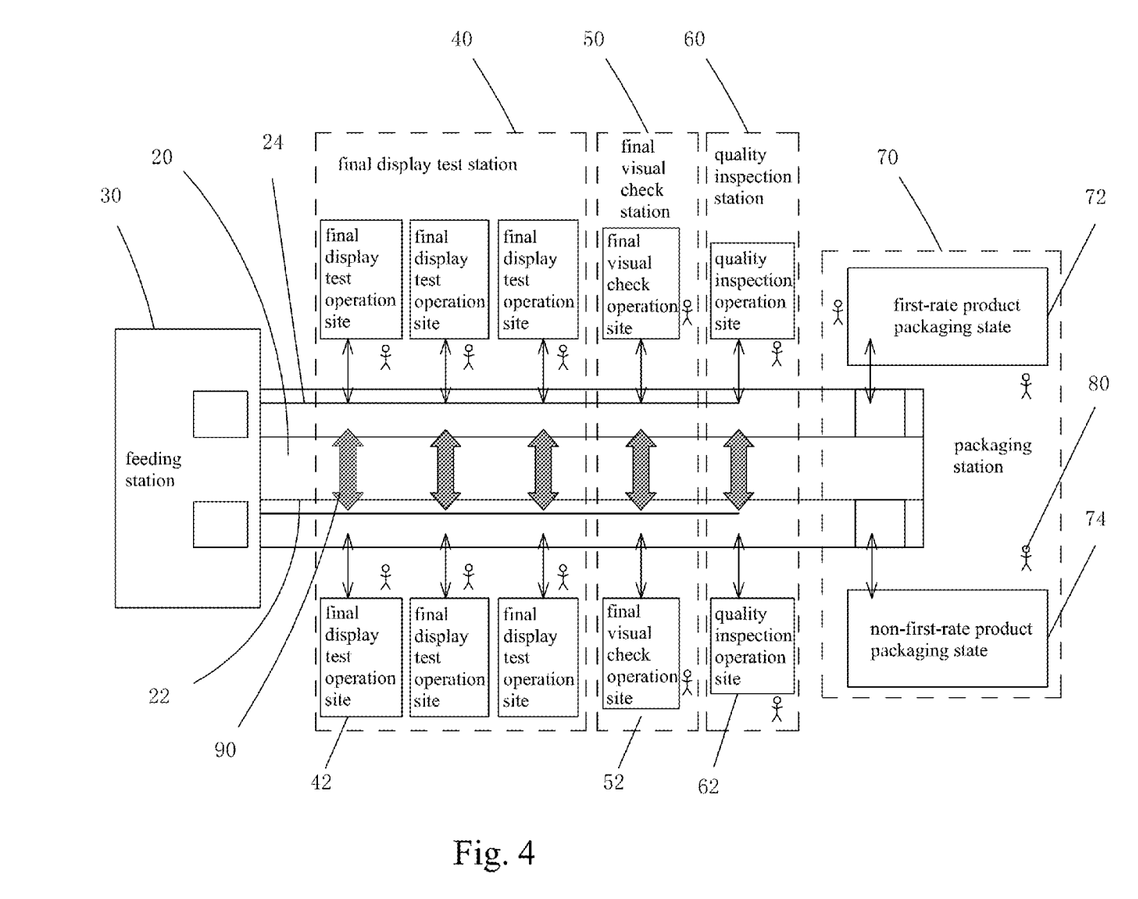
FIG. 4 is a schematic view showing an automatic inspection line for carrying out the method for inspecting a panel-bonding semi-finished product according to the present invention.

Referring to FIGS. 2-4, the present invention provides a method for inspecting a panel-bonding semi-finished product, which comprises the following steps:

Step 1: placing a panel-bonding semi-finished product on a tray (not shown) in a feeding station 30.

Specifically, an operator 80 of the feeding station 30 uses a feeding device that is commonly used in the industry to carry out de-packaging, posting, positioning, and transporting of the panel-bonding semi-finished product so as to place the panel-bonding semi-finished product on the tray. The posting operation determines and records the product classification of the panel-bonding semi-finished product.

The step can be directly jointed to a bonding operation process to form a single production line so as to increase operation efficiency and unwanted consequence caused by conveyance of the panel-bonding semi-finished product between various manufacturing operations.

The tray is of a size selected or determined according to the size of the panel-bonding semi-finished product and, specifically, comprises a tray body and a P-gamma chip test transducer (not shown) connected to the body. The tray body is provided with backlighting, a P-gamma chip signal generator, a relay contact, a P-gamma chip signal line, and two control buttons. The two control buttons are respectively an "activating tray backlighting button" and an "ejecting tray button".

Step 2: using a conveyance mechanism 20 to convey the tray and the panel-bonding semi-finished product placed thereon to a final display test station 40.

In the instant embodiment, the conveyance mechanism comprises a double-plus chain conveyor mechanism 20. The double-plus chain conveyor mechanism 20 comprises therein a double-plus chain operation procedure and the double-plus chain conveyor mechanism 20 is operating according to the double-plus chain operation procedure to effect positioning and conveyance of the panel-bonding semi-finished product by means of the double-plus chain conveyor mechanism 20 to carry the panel-bonding semi-finished product to stations to carry out associated inspections and tests.

The double-plus chain conveyor mechanism 20 comprises a circulation conveyance ladder 22. The circulation conveyance ladder 22 comprises two parallel conductor tracks 24. The feeding station 30 is located at one end of the circulation conveyance ladder 22 and the packaging station 70 is located at an opposite end of the circulation conveyance ladder 22. A final display test station 40, a final visual check station 50, and a quality inspection station 60 are arranged sequentially between the feeding station 30 and the packaging station 70. The final display test station 40 comprises a plurality of final display test operation sites 42. The final display test operation sites 42 are respectively set at two sides of the circulation conveyance ladder 22. The final visual check station 50 comprises two final visual check operation sites 52 that are arranged symmetrically on two sides of the circulation conveyance ladder 22. Each of the final visual check operation sites 52 comprises a barcode pasting machine. The quality inspection station 60 comprises two quality inspection operation sites 62 symmetrically set at two sides of the circulation conveyance ladder 22. The packaging station 70 comprises a first-rate product packaging state 72 and a non-first-rate product packaging state 74 respectively set at two sides of the circulation conveyance ladder 22. The first-rate product packaging state 72 and the non-first-rate product packaging state 74 each comprise an automatic packaging machine. The arrangement of the barcode pasting machines and the automatic packaging machines effectively increases operation efficiency, enhance throughput, and reduce manufacture cost.

Preferably, the final display test station 40 comprises six final display test operation sites 42. The six final display test operation sites 42 are arranged at two sides of the circulation conveyance ladder 22 in a symmetric manner. The requirement of inspection of each of the final display test operation sites 42 can be satisfied by assigning a single operator 80 thereto. The requirement of inspection of each of the final visual check operation sites 52 can be satisfied by assigning a single operator 80 thereto. The requirement of inspection of each of the quality inspection operation sites 62 can be satisfied by assigning a single operator 80 thereto. Thus, in the entire test and inspection operation of the panel-bonding semi-finished product, the final display test station 40, the final visual check station 50, and the quality inspection station 60 only need ten (10) operators 80 and compared to the conventional operations, eight (8) persons can be saved thereby reducing the labor cost, reducing the manufacture cost, and improving economic efficiency.

The tray is arranged on the double-plus chain conveyor mechanism 20 and is movable with the double-plus chain conveyor mechanism 20. The conductor tracks 24 supply electrical power to the tray, namely providing operation voltages to the backlighting and the P-gamma chip signal generator carried by the tray body to generate a backlighting signal and a P-Gamma signal for driving the liquid crystal panel. The voltage supplied through the conductor tracks 24 is 12V or 24V.

The specific operation of this step is that: the double-plus chain conveyor mechanism 20 uses the circulation conveyance ladder 22 to convey the tray and the panel-bonding semi-finished product placed on the tray to the corresponding final display test operation sites 42 of the final display test station 40.

Step 3: proceeding with a final display test on the panel-bonding semi-finished product and ending the test if the test fails and proceeding to the next step if the test passes.

In this step, the final display test is performed such that the operator 80 connects the relay contact to the conductor tracks 24 to proceed with the final display test and complete evaluation and posting of display classification. If the result of the test fails, the inspection of the panel-bonding semi-finished product is ended and if the result of test passes, a P-gamma chip signal line is connected to a circuit board of the panel-bonding semi-finished product; and at the same time, a P-gamma chip test transducer is positioned at the middle of the panel-bonding semi-finished product; and the "activating tray backlighting button" of the tray body is pressed down to activate the function of the tray body to adjust and reach the most user-fit color and resolution through software based automatic inspection and voltage adjustment.

Step 4: using the conveyance mechanism 20 to convey the tray and the panel-bonding semi-finished product positioned thereon and passing the final display test to a final visual check station 50.

The specific operation of this step is such that: the "ejecting tray button" of the tray body is pressed down and the double-plus chain conveyor mechanism 20 uses the circulation conveyance ladder 22 to convey the tray and the panel-bonding semi-finished product placed on the tray from the final display test station 40 to a corresponding final visual check operation site 52 of the final visual check station 50. During this step, the software based automatic inspection and voltage adjustment is still kept in operation for adjustment of color and resolution of the panel-bonding semi-finished product in order to effectively shorten the waiting time of the subsequent stations, increase the manufacture efficiency, and provide sufficient time for adjustment so that the software based automatic inspection and voltage adjustment can adjust and reach the most user-fit color and resolution thereby improving the displaying quality of the panel-bonding semi-finished product.

Step 5: proceeding with final visual check for the panel-bonding semi-finished product that passes the final display test and if the result of inspection fails, ending the inspection and if the result of inspection passes, then proceeding to the next step.

In this step, the operator 80 inspects the front appearance of the panel-bonding semi-finished product. If the inspection identifies abnormality, such as staining, existing on the front appearance of the panel-bonding semi-finished product, then a cleansing operation is carried out on the front side of the panel-bonding semi-finished product. The subsequent operation will be carried out after the cleansing has been done. If it is not possible to cleanse it, then the inspection of the panel-bonding semi-finished product is ended in order to ensure the quality of the panel-bonding semi-finished product. If the result of inspection satisfies the requirement standard, then based on the result of the final display classification evaluation, a classification barcode is printed with the barcode pasting machine and automatically pasted to the panel-bonding semi-finished product. And, after the tray body passes through the software based automatic inspection and voltage adjustment to reach the most user-fit color and resolution, the P-gamma chip signal line is removed from the circuit board of the panel-bonding semi-finished product to complete the processing.

In this step, the operator 80 uses the barcode pasting machine to print out the classification barcode and automatically paste it to the panel-bonding semi-finished product. The fully automatic arrangement allows to reduce the human labor devoted thereto and to further improve the operation efficiency, to lower down manufacture cost, and to further improve yield rate of products.

Through Step 3 to Step 5, the panel-bonding semi-finished product can complete the P-Gamma inspection and adjustment. In this period, checking of the outside appearance is also completed to prevent idleness of operators, pauses of the manufacture line caused by excessive length of the P-Gamma test operation and to increase the throughput and reduce the space requirement for the P-Gamma test.

Step 6: using the conveyance mechanism 20 to convey the tray and the panel-bonding semi-finished product positioned thereon and passing the final visual check to a quality inspection station 60.

The specific operation of this step is such that: the double-plus chain conveyor mechanism 20 uses the circulation conveyance ladder 22 to convey the tray and the panel-bonding semi-finished product placed on the tray from the final visual check station 50 to a corresponding quality inspection operation site 62 of the quality inspection station 60.

Step 7: proceeding with quality inspection on the panel-bonding semi-finished product that passes the final visual check and if the result of inspection fails, ending the inspection and if the result of inspection passes, then proceeding to the next step.

In this step, the operator 80 carries out a spot check on the panel-bonding semi-finished product that completes the final display test in Step 3 in order to improve the accuracy of inspection. The ratio of spot check is determined according to practical needs. Besides spot-checking the inspection result done in Step 3, spot-checking may be simultaneously on other items to ensure the good quality rate of the products shipped to the client.

Step 8: using the conveyance mechanism 20 to convey the tray and the panel-bonding semi-finished product positioned thereon and passing the quality inspection to a packaging station 70.

The specific operation of this step is such that: the double-plus chain conveyor mechanism 20 uses the circulation conveyance ladder 22 to convey the tray and the panel-bonding semi-finished product placed on the tray from the quality inspection station 60 to the corresponding one of the first-rate and non-first-rate product packaging states 72, 74 of the packaging station 70.

Step 9: proceeding with packaging of the panel-bonding semi-finished product passing the quality inspection.

In a preferred embodiment of the present invention, the operator 80 uses the automatic packaging machines to carry out packaging of the panel-bonding semi-finished product according to the display classification thereof. In other words, the panel-bonding semi-finished product is classified as a first-rate product or a non-first-rate product, which are packaged separately. With an operator 80 being assigned to dispose trays and spacers in coordination with the disposition of the panel-bonding semi-finished product that passes the quality inspection by the automatic packaging machine, the speed and quality of packaging can be enhanced, the operation efficiency can be improved, and the required number of operators can be reduced to thereby lower down the labor cost and manufacture cost.

It is noted that the circulation conveyance ladder 22 comprises adjustment mechanisms 90 that have functions of elevation, rotation, and conveyance and are arranged to respectively correspond to the final display test operation sites 42 of the final display test station 40, the final visual check operation sites 52 of the final visual check station 50, and the quality inspection operation sites 62 of the quality inspection station 60. The adjustment mechanisms 90 are operable to switch the locations of trays on the two sides of the circulation conveyance ladder 22. Specifically, the trays in the final display test operation sites 42 of the final display test station 40 that are symmetrically arranged on the two sides of the circulation conveyance ladder 22 can be switched in position; the trays in the final visual check operation sites 52 of the final visual check station 50 that are symmetrically arranged on the two sides of the circulation conveyance ladder 22 can be switched in position; and the trays in the quality inspection operation sites 62 of the quality inspection station 60 that are symmetrically arranged on the two sides of the circulation conveyance ladder 22 can be switched in position. As such, when one of the operation sites become abnormal and cannot operate normally, through switching of the trays as described above, the tray in the abnormal operation site can be switched to a normal operation site to complete the operation. In this way, the operation of the entire product line is not affected by any abnormal operation site and the manufacture efficiency can be maximized.

In summary, the present invention provides a method for inspecting a panel-bonding semi-finished product, which adopts a conveyance mechanism to achieve automatization of an inspection line, joints test operations of the panel-bonding semi-finished product to a main bonding line of the panel-bonding semi-finished product, adds barcode pasting machines and automatic packaging machines, make a P-gamma chip carrying out software based automatic inspection and voltage adjustment to reach the most user-fit color and resolution and in combination with a final display test and a final visual check, coordinate all operation stations to operate in synchronization with each other so as to satisfy the required P-gamma chip test of the industry, where the operators do not need to contact products so as to achieve the purposes of reducing labor and improving the product yield rate of the product throughput of the panel-bonding semi-finished product and also to meet the trend of development of large sizes, avoid influence of human factors on the product yield rate and product throughput, and increase economical advantage.

Based on the description given above, those having ordinary skills of the art may easily contemplate various changes and modifications of the technical solution and technical ideas of the present invention and all these changes and modifications are considered within the protection scope of right for the present invention.

What is claimed is:

1. A method for inspecting a panel-bonding semi-finished product, comprising the following steps:
   (1) placing a panel-bonding semi-finished product on a tray in a feeding station;
   (2) using a conveyance mechanism to convey the tray and the panel-bonding semi-finished product placed thereon to a final display test station;
   (3) proceeding with a final display test on the panel-bonding semi-finished product and ending the test if the test fails and proceeding to the next step if the test passes;
   (4) using the conveyance mechanism to convey the tray and the panel-bonding semi-finished product positioned thereon and passing the final display test to a final visual check station;
   (5) proceeding with final visual check for the panel-bonding semi-finished product that passes the final display test and if the result of inspection fails, ending the inspection and if the result of inspection passes, then proceeding to the next step;
   (6) using the conveyance mechanism to convey the tray and the panel-bonding semi-finished product positioned thereon and passing the final visual check to a quality inspection station;
   (7) proceeding with quality inspection on the panel-bonding semi-finished product that passes the final visual check and if the result of inspection fails, ending the inspection and if the result of inspection passes, then proceeding to the next step;
   (8) using the conveyance mechanism to convey the tray and the panel-bonding semi-finished product positioned thereon and passing the quality inspection to a packaging station; and
   (9) proceeding with packaging of the panel-bonding semi-finished product passing the quality inspection.

2. The method for inspecting a panel-bonding semi-finished product as claimed in claim 1, wherein step (1) comprises: carrying out de-packaging, posting, positioning, and conveyance of the panel-bonding semi-finished product and then placing the panel-bonding semi-finished product on the tray.

3. The method for inspecting a panel-bonding semi-finished product as claimed in claim 1, wherein the conveyance mechanism comprises a double-plus chain conveyor mechanism.

4. The method for inspecting a panel-bonding semi-finished product as claimed in claim 3, wherein the double-plus chain conveyor mechanism comprises a circulation conveyance, the circulation conveyance ladder comprising two parallel conductor tracks, the feeding station being located at one end of the circulation conveyance ladder and the packaging station being located at an opposite end of the circulation conveyance ladder, the final display test station, the final visual check station, and the quality inspection station being arranged sequentially between the feeding station and the packaging station, the final display test station comprising a plurality of final display test operation sites, the final display test operation sites being symmetrically set at two sides of the circulation conveyance ladder, the final visual check station comprising two final visual check operation sites that are arranged symmetrically on the two sides of the circulation conveyance ladder, each of the final visual check operation sites comprising a barcode pasting machine, the quality inspection station comprising two quality inspection operation sites symmetrically set at the two sides of the circulation conveyance ladder, the packaging station comprising a first-rate product packaging state and a non-first-rate product packaging state respectively set at the two sides of the circulation conveyance ladder, the first-rate product packaging state and the non-first-rate product packaging state each comprising an automatic packaging machine.

5. The method for inspecting a panel-bonding semi-finished product as claimed in claim 4, wherein the tray arranged on the double-plus chain conveyor mechanism and is movable with the double-plus chain conveyor mechanism and comprises a tray body and a P-gamma chip test transducer connected to the body, the tray body being provided with backlighting, a P-gamma chip signal generator, a relay contact, a P-gamma chip signal line, and two control buttons, the two control buttons being respectively an "activating tray backlighting button" and an "ejecting tray button".

6. The method for inspecting a panel-bonding semi-finished product as claimed in claim 5, wherein step (3) comprises: connecting the relay contact to the conductor tracks to proceed with the final display test and identifying and posting of display classification and if the result of the test fails, ending the inspection of the panel-bonding semi-finished product and if the result of test passes, connecting a P-gamma chip signal line of the tray to a circuit board of the panel-bonding semi-finished product and positioning at the same time a P-gamma chip test transducer at the middle of the panel-bonding semi-finished product and pressing down the "activating tray backlighting button" of the tray body to activate a function of the tray body to adjust and reach the most user-fit color and resolution through software based automatic inspection and voltage adjustment; and step (4) comprises: pressing down the "ejecting tray button" and conveying the tray and the panel-bonding semi-finished product placed on the tray to the final visual check station.

7. The method for inspecting a panel-bonding semi-finished product as claimed in claim 6, wherein step (5) comprises: inspecting a front appearance of the panel-bonding semi-finished product and if abnormality is identified, then carrying out a cleansing operation on the abnormality and if the abnormality is not cleanable, ending the inspection of the panel-bonding semi-finished product, if the abnormality is cleansed, a barcode machine being used to automatically paste a classification barcode according to the result of test of step (3) and after the tray body passes through the software based automatic inspection and voltage adjustment to reach the most user-fit color and resolution, removing the P-gamma chip signal line from the circuit board of the panel-bonding semi-finished product.

8. The method for inspecting a panel-bonding semi-finished product as claimed in claim 6, wherein in step (9), an automatic packaging machine is used to carry out packaging according to display classification of the panel-bonding semi-finished product.

9. The method for inspecting a panel-bonding semi-finished product as claimed in claim 4, wherein the circulation conveyance ladder comprises adjustment mechanisms that have functions of elevation, rotation, and conveyance and are arranged to respectively correspond to the final display test operation sites of the final display test station, the final visual check operation sites of the final visual check station, and the quality inspection operation sites of the quality inspection station, the adjustment mechanisms being operable to switch the locations of trays on the two sides of the circulation conveyance ladder.

10. The method for inspecting a panel-bonding semi-finished product as claimed in claim 4, wherein the final display test station comprises six final display test operation sites, the six final display test operation sites being arranged at two sides of the circulation conveyance ladder in a symmetric manner, the conductor tracks supplying electrical power to the tray, electrical voltage provided by the conductor tracks being 12V or 24V.

11. A method for inspecting a panel-bonding semi-finished product, comprising the following steps:
  (1) placing a panel-bonding semi-finished product on a tray in a feeding station;
  (2) using a conveyance mechanism to convey the tray and the panel-bonding semi-finished product placed thereon to a final display test station;
  (3) proceeding with a final display test on the panel-bonding semi-finished product and ending the test if the test fails and proceeding to the next step if the test passes;
  (4) using the conveyance mechanism to convey the tray and the panel-bonding semi-finished product positioned thereon and passing the final display test to a final visual check station;
  (5) proceeding with final visual check for the panel-bonding semi-finished product that passes the final display test and if the result of inspection fails, ending the inspection and if the result of inspection passes, then proceeding to the next step;
  (6) using the conveyance mechanism to convey the tray and the panel-bonding semi-finished product positioned thereon and passing the final visual check to a quality inspection station;
  (7) proceeding with quality inspection on the panel-bonding semi-finished product that passes the final visual check and if the result of inspection fails, ending the inspection and if the result of inspection passes, then proceeding to the next step;
  (8) using the conveyance mechanism to convey the tray and the panel-bonding semi-finished product positioned thereon and passing the quality inspection to a packaging station; and
  (9) proceeding with packaging of the panel-bonding semi-finished product passing the quality inspection; and
  wherein step (1) comprises: carrying out de-packaging, posting, positioning, and conveyance of the panel-bonding semi-finished product and then placing the panel-bonding semi-finished product on the tray;
  wherein the conveyance mechanism comprises a double-plus chain conveyor mechanism;
  wherein the double-plus chain conveyor mechanism comprises a circulation conveyance, the circulation conveyance ladder comprising two parallel conductor tracks, the feeding station being located at one end of the circulation conveyance ladder and the packaging station being located at an opposite end of the circulation conveyance ladder, the final display test station, the final visual check station, and the quality inspection station being arranged sequentially between the feeding station and the packaging station, the final display test station comprising a plurality of final display test operation sites, the final display test operation sites being symmetrically set at two sides of the circulation conveyance ladder, the final visual check station comprising two final visual check operation sites that are arranged symmetrically on the two sides of the circulation conveyance ladder, each of the final visual check operation sites comprising a barcode pasting machine, the quality inspection station comprising two quality inspection operation sites symmetrically set at the two sides of the circulation conveyance ladder, the packaging station comprising a first-rate product packaging state and a non-first-rate product packaging state respectively set at the two sides of the circulation conveyance ladder, the first-rate product packaging state and the non-first-rate product packaging state each comprising an automatic packaging machine;
  wherein the tray arranged on the double-plus chain conveyor mechanism and is movable with the double-plus chain conveyor mechanism and comprises a tray body and a P-gamma chip test transducer connected to the body, the tray body being provided with backlighting, a P-gamma chip signal generator, a relay contact, a P-gamma chip signal line, and two control buttons, the two control buttons being respectively an "activating tray backlighting button" and an "ejecting tray button";
  wherein step (3) comprises: connecting the relay contact to the conductor tracks to proceed with the final display test and identifying and posting of display classification and if the result of the test fails, ending the inspection of the panel-bonding semi-finished product and if the result of test passes, connecting a P-gamma chip signal line of the tray to a circuit board of the panel-bonding semi-finished product and positioning at the same time a P-gamma chip test transducer at the middle of the panel-bonding semi-finished product and pressing down the "activating tray backlighting button" of the tray body to activate a function of the tray body to adjust and reach the most user-fit color and resolution through software based automatic inspection and voltage adjustment; and step (4) comprises: pressing down the "ejecting tray button" and conveying the tray and the panel-bonding semi-finished product placed on the tray to the final visual check station;
  wherein step (5) comprises: inspecting a front appearance of the panel-bonding semi-finished product and if abnormality is identified, then carrying out a cleansing operation on the abnormality and if the abnormality is not cleanable, ending the inspection of the panel-bonding semi-finished product, if the abnormality is cleansed, a barcode machine being used to automatically paste a classification barcode according to the result of test of step (3) and after the tray body passes through the software based automatic inspection and voltage adjustment to reach the most user-fit color and resolution, removing the P-gamma chip signal line from the circuit board of the panel-bonding semi-finished product;
  wherein in step (9), an automatic packaging machine is used to carry out packaging according to display classification of the panel-bonding semi-finished product;
  wherein the circulation conveyance ladder comprises adjustment mechanisms that have functions of elevation, rotation, and conveyance and are arranged to respectively correspond to the final display test operation sites of the final display test station, the final visual check operation sites of the final visual check station, and the quality inspection operation sites of the quality inspection station, the adjustment mechanisms being operable to switch the locations of trays on the two sides of the circulation conveyance ladder; and wherein the final display test station comprises six final display test operation sites, the six final display test operation sites being arranged at two sides of the circulation conveyance ladder in a symmetric manner, the conductor tracks supplying electrical power to the tray, electrical voltage provided by the conductor tracks being 12V or 24V.

\* \* \* \* \*